United States Patent [19]

Maruyama et al.

[11] Patent Number: 5,270,439
[45] Date of Patent: Dec. 14, 1993

[54] METHOD OF PRODUCING A CURABLE COMPOSITION CONTAINING 4,4'-BIS(METHACRYLOYLTHIO)DIPHENYLSULFIDE

[75] Inventors: Satoshi Maruyama; Naoki Minorikawa; Tsutomu Arakawa, all of Kawasaki; Haruo Yoshida, Oita; Hirotaka Tagoshi, Oita; Kazuto Abe, Oita, all of Japan

[73] Assignee: Sumitomo Seika Chemicals Co., Ltd., Hyogo, Japan

[21] Appl. No.: 952,655

[22] Filed: Sep. 28, 1992

Related U.S. Application Data

[62] Division of Ser. No. 499,421, Jun. 20, 1990, Pat. No. 5,183,917.

[30] Foreign Application Priority Data

| Oct. 20, 1988 | [JP] | Japan | 63-26578 |
| Oct. 20, 1988 | [JP] | Japan | 63-265776 |
| Dec. 14, 1988 | [JP] | Japan | 63-315559 |
| Jun. 20, 1989 | [JP] | Japan | 1-157528 |
| Jul. 21, 1989 | [JP] | Japan | 1-190203 |

[51] Int. Cl.⁵ .................................. C08G 75/00
[52] U.S. Cl. .......................... 528/373; 529/272; 529/274; 529/293; 529/295; 529/295.5; 529/303; 529/375; 529/376; 529/392; 525/55; 525/132; 525/185; 525/189; 525/190
[58] Field of Search ............... 528/373, 375, 376, 392, 528/272, 274, 293, 295, 295.5, 303; 525/55, 132, 185, 189, 190

[56] References Cited

U.S. PATENT DOCUMENTS 4,388,450  6/1983  Crivello ......................... 525/502
4,810,812  3/1989  Matsuda et al. ................ 558/251

FOREIGN PATENT DOCUMENTS 273661   7/1988   European Pat. Off.
5328959  8/1978   Japan.
59164501 9/1984   Japan.
62283109 12/1987  Japan.

*Primary Examiner*—John Kight, III
*Assistant Examiner*—Sam A. Acquah
*Attorney, Agent, or Firm*—Sughrue, Mion, Zinn, Macpeak & Seas

[57] ABSTRACT

A method of producing a curable composition containing a prepolymer having a polythioether skeleton, characterized by comprising addition reacting (A) 4,4'-bis(methacryloylthio)-diphenylsulfide having the formula (I):

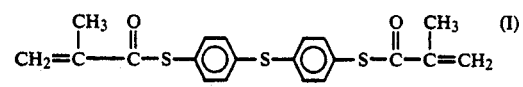

and (B) (ii) a polythiol having the formula (II):

$$R-(SH)_n \qquad (II)$$

wherein R is a polyvalent organic group composed of an aliphatic or aromatic hydrocarbon and n represents an integer of 2 or more, with the functional group equivalent ratio of the mercapto groups of the component (B) (ii) to the methacryloyl groups of the component (A) being from 0.02 to 1.01, in another vinyl monomer copolymerizable with 4,4'-bis(methacryloylthio)-diphenylsulfide having the above formula (I) in the presence of a base catalyst.

4 Claims, 2 Drawing Sheets

METHOD OF PRODUCING A CURABLE COMPOSITION CONTAINING 4,4'-BIS(METHACRYLOYLTHIO)DIPHENYLSULFIDE

This is a divisional of application Ser. No. 07/499,421 filed Jun. 20, 1990, now U.S. Pat. No. 5,183,917.

TECHNICAL FIELD

The present invention relates to a novel bifunctional polymerizable monomer capable of producing a transparent cured product having a high heat resistance, low water absorption, and high refractive index, more particularly, to 4,4'-bis(methacryloylthio)diphenylsulfide suitable as the starting material for paints, adhesives, cast molding materials, photosensitive resins, and optical materials, most particularly as the starting material for an optical material.

Furthermore, the present invention relates to a curable composition containing a prepolymer having a polythioether skeleton useful in the industrial fields of optical materials, coating agents, sealing agents, paints, and adhesives, particularly the field of optical materials, and a method of producing same. More particularly, it relates to a curable composition containing a prepolymer having a polythioether skeleton which gives a superior cured product having a high refractive index, low water absorption, and a high optical uniformity during polymerization, and a method of producing same.

BACKGROUND OF ART

A large number of derivatives of monofunctional methacrylic acid esters and polyfunctional methacrylic acid esters are known, and some of these esters are commercially produced and used as the starting materials for adhesives, paints, cast molding materials, and photosensitive materials, utilizing the high polymerizability thereof.

On the other hand, few derivatives of thiomethacrylic acid esters are known. For example, although phenylthiomethacrylate and 4-chlorophenylmethacrylate were synthesized by Jean Samrel et al (Journal of American Chemical Society (i. Am. Chem. Soc.), 86, 2509 (1958)], almost none of these thiomethacrylic acid esters have been utilized commercially.

In the prior art, as organic optical materials, polystyrene resins, polymethyl methacrylate resins, polycarbonate resins, and polymers of diethylene glycol and diallylcarbonate have been utilized, and since these have a desirable light weight, safety, workability, and dyeability, the demand therefore has increased.

Organic optical materials of the prior art, however, for example, polymethacrylate resins, have a high hygroscopicity as the resin characteristic, are susceptible to changes in shape or refractive index, and are unstable as optical materials. On the other hand, polystyrene resins and polycarbonate resins have drawbacks such as an optical birefringence, generation of scattered light, and loss of transparency with time. Further, the application of polymers of diethylene glycol diallylcarbonate per se as the optical material is limited due to the low refractive index (refractive index=1.499) thereof.

To eliminate these drawbacks, various resins for optical materials have been proposed, and examples of these proposals include, for example, Japanese Unexamined Patent Publications (Kokai) Nos. 57-28115, 57-28116, 59-184210, 60-7314, 60-179406, 60-217301, 60-186514, 60-166307, 60-103301, 60-124607, 62-232414, 62-235901, 62-267316, 63-15811, 63-46213, 63-72707, 63-75022, 63-113012, 63-130614, 63-130615, 63-170401, 63-170404, 63-191813, 63-248811, 63-251408t 63-268707, and 64-54021, Japanese Examined Patent Publication (Kokoku) Nos. 63-45081 and 63-45082, and Japanese Unexamined Patent Publication (Kokai) Nos. 59-164501, 60-217299, 61-16901, 62-283109, 62-287316 and 63-162702. The cured products obtained by these prior arts, however, are not satisfactory as optical materials because they are optically nonuniform, suffer from a severe weathering coloration, and lack dimensional stability.

Also, curable compositions of polyene and polythiol are disclosed in Japanese Patent Publication (Kokoku) No. 53-28959, Japanese Unexamined Patent Publications (Kokai) Nos. 53-134096, 57-125025, 57-130572, 58-80317, but in these prior arts, due to the action of the mercapto groups as the chain transfer agent, a problem arises in that the polymerization tends to proceed even under storage in a dark place. Further, when the polyene compound is a (meth)acrylic acid derivative, a mutual polymerization between polyene compounds is liable to occur, whereby the mercapto groups are left, and thus problems arise such as an insufficient curing of the polymerized cured product, a lower chemical resistance, and a non-homogeneity of the cured product.

DISCLOSURE OF THE INVENTION

An object of the present invention is to provide a 4,4'-bis(methacryloylthio)diphenylsulfide for the preparation of a well-balanced resin having a high refractive index, a high heat resistance, and a low water absorption, and suitable not only as an optical material, but also having an excellent curability and able to be used as the starting material for paints, adhesives, cast molding materials, and photosensitive resins, by overcoming the drawbacks of the prior art resin for optical materials as described above.

Another object of the present invention is to provide a curable composition suitable for the preparation of a cured product having various well-balanced properties such as an optical uniformity and low water absorption and heat resistance, which is made suitable as an optical material by overcoming the drawbacks of the resin for optical material of the prior art as described above, and which can be used as a material such as coating agent, sealing agent, paint, and adhesive.

Other objects and advantages of the present invention will be apparent from the following description.

In accordance with the present invention, there is provided a 4,4'-bis(methacryloylthio)diphenylsulfide having the formula (I):

In accordance with the present invention, there is also provided a curable composition (sometimes referred to as "the first curable composition" hereinbelow), comprising:

(A) 4,4'-bis(methacryloylthio)diphenylsulfide having the above formula (I) and (B) (i) another vinyl monomer copolymerizable with 4,4'-bis(methacryloylthio)diphenylsulfide having the above formula (I), and (ii) a polythiol represented by the formula (II):

R—(SH)$_n$  (II)

wherein R is apolyvalent organic group and n represents an integer of 2 or more, wherein the content of the component (B)(i), when the component (B)(i) is present, in the total amount of said components (A), (B)(i) and (B)(ii) is 10 to 90% by weight, and the functional group equivalent ratio of the mercapto groups of the component (B)(ii), when the component (B)(ii) is present, to the methacryloyl groups of the component (A) is from 0.02 to 1.01.

In accordance with the present invention, there is further provided a curable composition (sometimes referred to as "the second curable composition" hereinbelow) comprising:

a prepolymer having a polythioether skeleton obtained by the addition reaction of:

(A) 4,4'-bis(methacryloylthio)diphenylsulfide having the above formula (I) and (B) (ii) a polythiol having the formula (II):

R—(SH)$_n$  (II)

wherein R is a polyvalent organic group composed of an aliphatic or aromatic hydrocarbon and n represents an integer of 2 or more, and (B) (i) another polymerizable monomer copolymerizable with 4,4'-bis(methacryloylthio)diphenylsulfide having the above formula (I).

In accordance with the present invention, there is still further provided a method of producing a curable composition containing a prepolymer having a polythioether skeleton, which comprises subjecting (A) 4,4'-bis(methacryloylthio)diphenylsulfide having the above formula (I) and (B) (ii) a polythiol having the formula (II):

Rpl3 (SH)$_n$  (II)

wherein R is a polyvalent organic group composed of an aliphatic or aromatic hydrocarbon and n represents an integer of 2 or more, to an addition reaction, where the functional group equivalent ratio of the mercapto groups of the component (B)(ii) to the methacryloyl groups of the component (A) is from 0.02 to 1.01, in another polymerizable monomer copolymerizable with 4,4'-bis(methacryloylthio)diphenylsulfide having the above formula (I) in the presence of a base catalyst.

BRIEF DESCRIPTION OF THE DRAWINGS

The present invention will be better understood from the description set forth below with reference to the accompanying drawings, wherein.

BEST MODE OF CARRYING OUT THE INVENTION

The 4,4'-bis(methacryloylthio)diphenylsulfide having the above-formula (I) can be obtained by, for example, a method in which 4,4'-dimercaptodiphenylsulfide having the formula (III):

is converted to an alkali metal salt in an aqueous solution containing an alkali metal oxide such as sodium hydroxide and potassium hydroxide, dissolved therein, then a generally employed phase transfer catalyst such as tetraethylammonium bromide and trimethylmonoethylammonium sulfate, and an organic solvent stable in alkalis and acids and without a water solubility such as dichloromethane, carbon tetrachloride, 1,2-dichloroethane, diethyl ether, and benzene, are added at a substantially equal volume ratio to the solution, and a methacrylic acid halide such as methacrylic acid chloride and methacrylic acid bromide is gradually added dropwise to this two phase systems reaction mixture.

The amount of the phase transfer catalyst to be used in this reaction is preferably from 0.00001 mole equivalent to 0.05 mole equivalent, more preferably from 0.0001 to 0.01 mole, relative to the 4,4'-dimercaptodiphenylsulfide. If the phase transfer catalyst is more than 0.05 mole equivalent, this is not only uneconomical but also it becomes undesirably difficult to separate the aqueous layer from the organic layer in the purification step after the reaction. On the other hand, if the amount of the phase transfer catalyst is less than 0.00001 mole equivalent, the reaction rate becomes undesirably slow.

Also, as another method of synthetising 4,4'-bis(methacryloylthio)diphenylsulfide represented by the above formula (I), a method is known in which 4,4'-dimercaptodiphenylsulfide is converted into an alkali metal salt by the same method as in the above-described method, and then a methacrylic acid halide is gradually added dropwise directly to the solution.

The amount of the alkali metal hydroxide to be used in the methods as described above is preferably from 2-fold equivalent to 20-fold equivalent, more preferably from 3-fold to 15-fold, relative to the 4,4'-dimercaptodiphenylsulfide. The amount of the methacrylic acid halide employed is preferably from 2-fold equivalent to 8-fold equivalent, more preferably from 2-fold equivalent to 5-fold equivalent, relative to the 4,4'-dimercaptodiphenylsulfide. If the amounts of these alkali metal hydroxide and methacrylic acid halide are more than the ranges specified above, they are not economical, and if less, the yield of 4,4'-bis(methacryloylthio)diphenylsulfide will be undesirably lowered. The reaction temperature during the synthesis is preferably maintained at −10° C. to 50° C., more preferably 0° C. to 40° C. If the reaction temperature is higher than 50° C., the 4,4'-bis(methacryloylthio)diphenylsulfide is frequently thermally polymerized and undesirably gelled, and if the reaction temperature is lower than −10° C., precipitation of an alkali metal salt of 4,4'-dimercaptodiphenylsulfide occurs, and further, the reaction mixture has a higher viscosity.

The 4,4'-bis(methacryloylthio)diphenylsulfide according to the present invention is a colorless solid having a relatively lower melting point (61°–61.5° C.) and soluble in organic solvents generally used, such as acetone, chloroform and diethyl ether. Also, the 4,4'-bis(methacryloylthio)diphenylsulfide of the present invention has a very good compatibility with other polymerizable monomers having an olefinic double bond, and is a useful curable monomer as one component of a curable composition.

The 4,4'-bis(methacryloylthio)diphenylsulfide of the present invention contains sulfur atoms within the molecule, and therefore, the cured product obtained by a polymerization curing thereof alone has an extremely high refractive index. Therefore, by a polymerization curing obtained by mixing 4,4'-bis(methacryloylthio)diphenylsulfide with another polymerizable monomer having an olefinic double bond, which gives a low refractive index, the refractive index of the cured product can be easily enhanced.

The 4,4'-bis(methacryloylthio)diphenylsulfide represented by the above formula (I) to be used as the component (A) in the present invention has specific features such that it can be easily mixed with other organic compounds, and has a very low affinity for water and very high refractive index (refractive index = 1.689). Therefore, by mixing this component (A) with another vinyl monomer copolymerizable with component (A) and a polythiol at a formulation ratio corresponding to the purpose, an improvement of the refractive index and reduction of the water absorption of the cured product obtained by curing the composition can be effected.

Other vinyl monomers copolymerizable with the component (A) to be used as the component (B) in the present invention are not particularly limited, provided that they are compatible with the component (A). Examples of other vinyl monomers copolymerizable with the component (A) include unsaturated fatty acid esters, aromatic vinyl compounds, unsaturated fatty acids and derivatives thereof, unsaturated dibasic acids and derivatives thereof, and vinyl cyanide compounds such as (meth)acrylonitrile.

Unsaturated fatty acids and derivatives thereof may include (meth)acrylamides such as (meth)acrylamide, N,N-dimethyl(meth)acrylamide, N,N-diethyl(meth)acrylamide and the like, and unsaturated fatty acids such as (meth)acrylic acids, furthermore, unsaturated fatty acid esters, for example, alkyl (meth)acrylates such as methyl (meth)acrylate (referring to both methyl acrylate and methyl methacrylate in the present specification; the same in other cases), ethyl (meth)acrylate, butyl (meth)acrylate, 2-ethylhexyl (meth)acrylate, octyl (meth)acrylate, dodecyl (meth)acrylate, octadecyl (meth)acrylate, cyclohexyl (meth)acrylate, methylcyclohexyl (meth)acrylate, (iso)bornyl (meth)acrylate, adamantyl (meth)acrylate and the like; aromatic esters of acrylic acid such as phenyl (meth)acrylate, benzyl (meth)acrylate, 1-naphthyl (meth)acrylate, fluorophenyl (meth)acrylate, chlorophenyl (meth)acrylate, bromophenyl (meth)acrylate, tribromophenyl (meth)acrylate, methoxyphenyl (meth)acrylate, cyanophenyl (meth)acrylate, biphenyl (meth)acrylate, bromobenzyl (meth)acrylate and the like; haloalkyl (meth)acrylates such as fluoromethyl (meth)acrylate, chloromethyl (meth)acrylate, bromoethyl (meth)acrylate, trichloromethyl (meth)acrylate and the like; 2-hydroxyethyl (meth)acrylate, (meth)acrylic acid polyethylene glycol esters, etc.; and otherwise, (meth)acrylic acid esters such as glycidyl (meth)acrylate, and alkylamino (meth)acrylate. Also, α-substituted acrylic acid esters such as α-fluoroacrylic acid esters, α-cyanoacrylic acid esters and the like may be included.

As aromatic vinyl compounds, styrene, or α-substituted styrenes such as α-methylstyrene, α-ethylstyrene, α-chlorostyrene and the like, nucleus-substituted styrenes such as fluorostyrene, chlorostyrene, bromostyrene, chloromethylstyrene, and methoxystyrene may be included.

Unsaturated dibasic acids and derivatives thereof may include N-substituted maleimides such as N-methylmaleimide, N-ethylmaleimide, N-butylmaleimide, N-cyclohexylmaleimide, N-phenylmaleimide, N-methylphenylmaleimide, N-chlorophenylmaleimide, N-carboxyphenylmaleimide and the like, maleic acid, maleic anhydride, and fumaric acid.

In addition to the monofunctional vinyl monomers, as other vinyl monomers copolymerizable with the component (A) to be used in the present invention, crosslinkable polyfunctional monomers may be included. For example, there may be included difunctional crosslinkable monomers, including di(meth)acrylates such as ethylene glycol di(meth)acrylate, diethylene glycol di(meth)acrylate, triethylene glycol di(meth)acrylate, tetraethylene glycol di(meth)acrylate, tripropylene glycol di(meth)acrylate, 1,3-butylene glycol di(meth)acrylate, 1,4-butane diol di(meth)acrylate, 1,5-pentane diol di(meth)acrylate, 1,6-hexane diol di(meth)acrylate, neopentyl glycol di(meth)acrylate, hydroxypivalic acid neopentyl glycol ester di(meth)acrylate, oligoester di(meth)acrylate, polybutadiene di(meth)acrylate, 2,2-bis(4-(meth)acryloyloxyphenyl)propane, 2,2-bis(4-(ω-(meth)acryloyloxypolyethoxy)phenyl)propane, 2,2-bis(4-(ω-(meth)acryloyloxypolyethoxy)dibromophenyl)propane, 2,2-bis(4-(ω-(meth)acryloyloxypolypropoxy)phenyl)propane, bis(4-(w-(meth)acryloyloxypolyethoxy)phenyl)methane and the like, diallyl phthalate, diallyl isophthalate, diallyl terephthalate, diallyl carbonate, diethylene glycol diallyl carbonate, divinylbenzene, divinylbiphenyl, N,N'-m-phenylenebismaleimide, etc.; trifunctional crosslinkable monomers such as trimethylolethane tri(meth)acrylate, trimethylolpropane tri(meth)acrylate, pentaerythritol tri(meth)acrylate, tri(meth)allyl isocyanurate, triallyl trimellitate, and diallyl chlorendate; and tetrafunctional crosslinkable monomers such as pentaerythritol tetra (meth)acrylate. Other vinyl monomers copolymerizable with the component (A) as mentioned above Kidy be used as a mixture of two or more kinds thereof.

As the polythiols of the component (B)(ii) represented by the above formula (II), aliphatic polythiols with n being an integer of 2 or more, preferably 2 to 5, or aromatic polythiols may be preferably used, particularly preferably aliphatic polythiols with n being an integer of 2 to 5. Representative examples of polythiols may include dithiols such as 9,10-anthracenedimethanethiol, 1,11-undecanedithiol, 4-ethylbenzene-1,3-dithiol, 1,2-ethane dithiol, 1,8-octane dithiol, 1,18-octadecane dithiol, 2,5-dichlorobenzene-1,3-dithiol, 1,3-(4-chlorophenyl)propane2,2-dithiol, 1,1-cyclohexanedithiol, 1,2-cyclohexanedithiol, 1,4-cyclohexanedithiol, 1,1-cycloheptanedithiol, 1,1-cyclopentanedithiol, 4,8-dithioundecane1,11-dithiol, dithiopentaerythritol, dithiothreitol, 1,3-diphenylpropane-2,2-dithiol, 1,3-dihydroxy-2-propyl2',3'-dimercaptopropyl ether, 2,3-dihydroxypropyl2',3'-dimercaptopropyl ether, 2,6-dimethyloctane-2,6dithiol, 2,6-dimethyloctane-3,7-dithiol, 2,4-dimethylbenzene-1,3-dithiol, 4,5-dimethylbenzene-1,3-dithiol, 3,3-dimethylbutane-2,2-dithiol, 2,2-dimethylpropane1,3-dithiol, 1,3-di(4-methoxyphenyl)propane-2,2-dithiol, 3,4-dimethoxybutane-1,2-dithiol, 10,11-dimercaptoundecanoic acid, 6,8-dimercaptooctanoic acid, 2,5-dimercapto-1,3,4-thiadiazole, 2,2'-dimercaptobiphenyl, 4,4'-dimercaptobiphenyl, 4,4'-dimercaptobibenzyl, 3,4-dimercaptobutanol, 3,4-dimercaptobutyl acetate, 2,3-dimercapto-1-propanol, 1,2-dimercapto-1,3-butane diol, 2,3-dimercaptopropionic acid, 1,2-dimercaptopropyl methyl ether, 2,3-dimercaptopropyl-2',3'-dimethoxypropyl ether, 3,4-thiophenedithiol, 1,10-decane dithiol, 1,12-dodecane dithiol, 3,5,5-trimethylhexane-1,1-dithiol, 2,5-toluenedithiol, 3,4-toluenedithiol, 1,4-naphthalenedithiol, 1,5-naphthalenedithiol, 2,6-naphthalenedithiol, 1,9-nonanedithiol, norbornene2,3-dithiol, bis(2-mercaptoisopropyl)ether, bis(11mercaptoundecyl)sulfide, bis(2-mercaptoethyl)ether, bis(2-mercaptoethyl)sulfide, bis(18-mercaptooctadecyl)sulfide, bis(8-mercaptooctyl)sulfide, bis(12-mercaptodecyl)sulfide, bis(9-mercaptononyl)sulfide, bis(4-mercaptobutyl)sulfide, bis(3-mercaptopropyl)ether, bis(3-mercaptopropyl)sulfide, bis(6-mercaptohexyl)sulfide, bis(7-mercaptoheptyl)sulfide, bis(5-mercaptopentyl)sulfide, 2,2'-bis(mercaptomethyl)acetic acid, 1,1-bis(mercaptomethyl)cyclohexane, bis(mercaptomethyl)durene, phenylmethane-1,1-dithiol, 1,2-butanedithiol, 1,4-butanedithiol, 2,3-butanedithiol, 2,2-butanedithiol, 1,2-propanedithiol, 1,3-propanedithiol, 2,2-propanedithiol, 1,2-hexanedithiol, 1,6-hexanedithiol, 2,5-hexanedithiol, 1,7-heptanedithiol, 2,6-heptanedithiol, 1,5-pentanedithiol, 2,4-pentanedithiol, 3,3-pentanedithiol, 7,8-heptadecanedithiol, 1,2-benzenedithiol, 1,3-benzenedithiol, 1,4-benzenedithiol, 2-methylcyclohexane-1,1-dithiol, 2-methylbutane-2,3-dithiol, ethylene glycol dithioglycolate, ethylene glycol bis(3-mercaptopropionate) and the like; and otherwise trithiols such as 1,2,3-propanetrithiol, 1,2,4-butanetrithiol, trimethylolpropanetrithiol glycolate, trimethylolpropane tris(3-mercaptopropionate), pentaerythritol trithioglycolate, pentaerythritol tris(3-mercaptopropionate), 1,3,5-benzenetrithiol, 2,4,6-mesitylenetrithiol and the like; and neopentanetetrathiol, 2,2'-bis(mercaptomethyl)-1,3-propanedithiol, pentaerythritol tetrakis(3-mercaptopropionate), 1,3,5-benzenetrithiol, 2,4,6-toluenetrithiol, 2,4,6-mesitylenetrithiol; and so on.

The polythiol of the component (B)(ii) as exemplified above can be used either alone or as a mixture of two or more kinds thereof. By mixing the polythiol with the component (A) and the component (B)(i) at a formulation ratio corresponding to the purpose, an improvement of the impact resistance of the cured product obtained by curing the composition can be effected.

As mentioned above, the first curable composition according to the present invention comprises the component (A) having the components (B)(i) and/or B(ii) formulated therein. When the first curable composition according to the present invention contains the component (B)(i), i.e., the components (A) and (B)(i) or the components (A), (B)(i) and (B)(ii), preferably these components formulated such that the content of the component (B)(i) (i.e., another vinyl monomer copolymerizable with the component (A)) in the total amount of the components (A), (B)(i) and B(ii) is 10 to 90% by weight, more preferably 15 to 85% by weight. On the other hand, when the component (B)(ii) is contained, i.e., when the components (A) and (B)(ii) or the components (A), (B)(i) and B(ii) are included, the component (B)(ii) is preferably formulated such that the functional group equivalent ratio of the mercapto groups of the component (C) to the methacryloyl groups of the component (A) is from 0.02 to 1.01, more preferably 0.01 to 1.0. The remainder is the component (A).

When the amount of the component (B)(i) in the first curable composition of the present invention is smaller than 10% by weight, the desired optical characteristics, water absorbability, heat resistance or impact resistance cannot be expected from the cured product obtained by curing when the component (B)(ii) is not used, and the mechanical characteristics are poor and an embrittlement of the cured product obtained by curing may occur when the component (B)(ii) is used. On the other hand, when the amount of the component (B)(i) is more than 90% by weight, a problem arises in that one of the optical characteristics, water absorption and heat resistance becomes poor when the component (B)(i) is not used, and the mechanical strength such as the impact resistance is unpreferably lowered. The amount of the component (B)(i) may be freely varied within the range of 10 to 90% by weight based upon, for example, the purpose of the application and the kinds of the vinyl monomers used in the composition.

Contrary to the above, when the functional group equivalent ratio of the component (B)(ii) mercapto groups to the component (A) methacryloyl groups is smaller than 0.02, the cured product becomes brittle, and is not practical. On the other hand, when the functional group equivalent ratio is greater than 1.01, when the curable composition is cured, not only does a polymerization irregularity with unreacted mercapto groups occur but also the crosslinking is poor, whereby the hardness, etc., of the cured product will be greatly lowered.

The first curable composition of the present invention can be cured by radical polymerization. The radical polymerization initiator to be used in radical polymerization may be any radical polymerization which can form radicals by heat, microwaves, IR-rays or UV-rays, and can be selected depending on the use and purpose of the curable composition.

Examples of the radical polymerization initiators which can be used during a polymerization with heat, microwaves, and UV-rays include azo compounds such as 2,2'-azobisisobutyronitrile, 2,2'-azobisisovaleronitrile, 2,2'-azobis(2,4-dimethylvaleronitrile) and the like; ketone peroxides such as methyl ethyl ketone peroxide, methyl isobutyl ketone peroxide, cyclohexanone peroxide, acetylacetone peroxide and the like; diacyl peroxides such as isobutyryl peroxide, 2,4-dichlorobenzoyl peroxide, o-methylbenzoyl peroxide, lauroyl peroxide, p-chlorobenzoyl peroxide and the like; hydroperoxides such as 2,4,4-trimethylpentyl-2-hydroperoxide, diisopropylbenzene peroxide, cumene hydroperoxide, t-butyl peroxide and the like; dialkylperoxides such as dicumyl peroxide, t-butylcumyl peroxide, di-t-butylperoxide, tris(t-butylperoxy)triazine and the like; peroxyketals such as 1,1-di-t-butylperoxycyclohexane, 2,2-di(t-butylperoxy)butane and the like; alkyl peresters such as t-butylperoxypivalate, t-butylperoxy-2-ethylhexanoate, t-butylperoxyisobutyrate, di-t-butylperoxyhexahydroterephthalate, di-t-butylperoxyazelate, t-butylperoxy-3,5,5-trimethylhexanoate, t-butylperoxyacetate, t-butylperoxybenzoate, di-t-butylperoxytrimethyladipate and the like; percarbonates such as diisopropylperoxydicarbonate, di-secbutylperoxydicarbonate, t-butylperoxyisopropylcarbonate and the like.

Examples of the radical polymerization initiators to be used during polymerization with Uv-rays include carbonyl compounds such as acetophenone, 2,2-dimethoxy2-phenylacetophenone, 2,2-diethoxyacetophenone, 4-isopropyl-2-hydroxy-2-methylpropiophenone, 2-hydroxy-2-methylpropiophenone, 4,41-bis(diethylamino)benzophenone, benzophenone, methyl(o-benzoyl)benzoate, 1-phenyl-1,2-propanedione-2-(o- ethoxycarbonyl)oxime, 1-phenyl-1,2-propenedione-2-(o-benzoyl)oxime, benzoin, benzoin methyl ether, benzoin ethyl ether, benzoin isopropyl ether, benzoin isobutyl ether, benzoin octyl ether, benzyl, benzyl dimethyl ketal, benzyl diethyl ketal, diacetyl and the like, anthraquinone or thioxanthone derivatives such as methylanthraquinone, chloroanthraquinone, chlorothioxanthone, 2-methylthioxanthone, 2-isopropylthioxanthone and the like; and sulfur compounds such as diphenyldisulfide, and dithiocarbamate.

The amount of the radical polymerization initiator varies depending on the kind of the radical polymerization initiator, the use of the curable composition, and the kinds and the composition ratio of the monomers charged, and therefore, cannot be determined unconditionally, but preferably is from 0.001 to 20 mole %, based on the total amount of the components (A), (B)(i) and (B)(ii), more preferably from 0.01 to 10 mole %. When the amount of the radical polymerization initiator is less than 0.001 mole %, the polymerization substantially does not proceed, and when the amount is over 20 mole %, not only it is uneconomical but in some cases foaming may occur during polymerization, or the molecular weight of the cured product obtained by polymerization may be reduced.

The second curable composition of the present invention may be prepared by previously synthesising the prepolymer having a polythioether skeleton and mixing same with another polymerizable monomer of the component (B)(i), or the prepolymer may be prepared directly by reacting 4,4'-bis(methacryloylthio)diphenylsulfide of the component (A) represented by the above formula (I) and a polythiol of the component (B)(ii) represented by the above formula (II) in another polymerizable monomer of the component (B)(i), but preferably the latter method, which involves simple preparation steps of the curable composition, is used.

When preparing the curable composition by mixing the prepolymer having a polythioether skeleton and another polymerizable monomer of the component (B)(i), the prepolymer having a polythioether skeleton is synthesised by previously subjecting 4,4'-bis(methacryloylthio)diphenylsulfide represented by the above formula (I) to be used as the component (A) and a polythiol represented by the above formula (II) to be used as the component (B)(ii).

When carrying out the addition reaction between 4,4'-bis(methacryloylthio)diphenylsulfide represented by the above formula (I) to be used as the component (A) and a polythiol represented by the above formula (II) to be used as the component (B)(ii), the functional group equivalent ratio of the mercapto groups of the component (B)(ii) to the methacryloyl groups of the component (A) is preferably from 0.02 to 1.01, particularly from 0.05 to 0.60. If the functional group equivalent ratio of the mercapto groups of the component (B)(ii) to the methacryloyl group of the component (A) is less than 0.02, the cured product is generally brittle and cannot provide a sufficient impact resistance. On the other hand, if the functional group equivalent ratio of the mercapto groups of the component (B)(ii) to the methacryloyl group of the component (A) is more than 1.01, problems arise such as a lowering of the stability of the composition due to the unreacted mercapto groups, an excessive elevation of the composition viscosity, and a nonhomogeneity of the cured product due to a nonuniformization of the polymerization reaction.

The addition reaction of the component (A) and the component (B)(ii) is carried out in a relatively lower boiling solvent, including ether solvents such as diethyl ether, ethylene glycol dimethyl ether, and tetrahydrofuran, aromatic hydrocarbon solvents such as benzene and toluene, and a chlorine type solvent such as dichloromethane, carbon tetrachloride, in the presence of a base catalyst. After completion of the reaction, a prepolymer having a polythioether skeleton can be obtained by removing the solvent. As the base catalyst for the addition reaction, a basic ion-exchange resin, potassium-t-butoxide, phosphine compound, and amine compound can be used, particularly preferably phosphine compound or amine compound is used.

Examples of the phosphine compounds include triphenylphosphine, tri-n-butylphosphine, triethylphosphine and the like, and examples of the amine compounds include pyridine, N,N-dimethylaniline, N,N-diethylaniline, trimethylamine, triethylamine, tri(n-propyl)amine, tri(iso-propyl)amine, tri(n-butyl)amine, tri(iso-butyl)amine, tri(sec-butyl)amine, dimethylethylamine, diethylmethylamine, diethylamine, triethanolamine, dimethylethanolamine, monomethyldiethanolamine and the like.

These base catalysts may be used either alone or in combination, and the amounts used differ depending on the kind of the component (B)(ii) and amount used, and therefore, cannot be defined unconditionally, but preferably is 0.01 to 3% by weight, more preferably 0.03 to 1% by weight, based on the total amount of the component (A) and the component (B)(ii). When the amount of the base catalyst is less than 0.01% by weight, substantially no action of the catalyst is obtained, whereby a frequent homopolymerization of the methacryloyl groups of the component (A) will occur. On the other hand, when the amount of the base catalyst exceeds 3% by weight, not only is no effect obtained by using it in a large amount, but also coloration occurs during polymerization. Also, even if the base catalyst after the reaction is removed, it is undesirable because a large amount of removing agent is required.

In the addition reaction between the component (A) and the component (B)(ii), when a high boiling solvent is used, when the method using heating is employed during the solvent removal, if the component (A) remains, gelation through a homopolymerization of the component (A) will occur.

To prevent gelation, a phenol type or amine type inhibitor can be added within the range which does not interfere with the polymerization between other polymerizable monomers in the next step. Also, when the removal of the base catalyst for the addition reaction is required, known methods such as adsorption, extraction, and vacuum aspiration are applicable within the range which does not affect polymerization in the next step. Particularly, for a removal of amine compounds, the adsorption removal method with neutral, acidic alumina and acidic ion-exchange resin is applicable, and when the amine compound is a low boiling amine compound, the removal method by vacuum aspiration can be utilized.

The temperature when carrying out the addition reaction differs depending on the kind and amount formulated of the component (B)(ii), or the kind and amount of the base catalyst used, and therefore, cannot be defined unconditionally, but preferably is 0° to 100° C., more preferably 20° to 60° C. Even if the addition reaction temperature exceeds 100° C., a homopolymerization of the component (A) can be prevented in some cases, depending on the kind and amount of the base catalyst employed, but frequently gelling occurs. On the other hand, the reaction proceeds even below 0° C., but the reaction rate is very slow and not desirable in production.

During the addition reaction, to prevent a formation of disulfide by an autooxidation of the component (B)(ii), it is preferable to carry out the addition reaction in an inert gas atmosphere.

The prepolymer having a polythioether skeleton thus obtained has a structure capped at the molecular terminal ends with polymerizable vinyl groups, and has an excellent storage stability.

The prepolymer having a polythioether skeleton obtained as described above is mixed with the another polymerizable monomer of the component (B)(i).

The formulation ratio of the prepolymer having a polythioether skeleton and other polymerizable monomers desirably comprise 30 to 90% by weight of the prepolymer having a polythioether skeleton and 10 to 70% by weight of other polymerizable monomers, preferably 50 to 85% by weight of the prepolymer having a polythioether skeleton and 15 to 50% by weight of other polymerizable monomers. When the amount of the prepolymer having a polythioether skeleton formulated is lower than 30% by weight, the property of a high refractive index, which is the greatest specific feature, cannot be obtained.

On the other hand, when the amount of the prepolymer having a polythiol skeleton formulated is more than 90% by weight, the composition has a higher viscosity, and thus becomes difficult to handle, which is undesirable in production when applied in industry.

The mixing of the prepolymer having a polythioether skeleton with other polymerizable monomers, can be carried out by methods conventionally well known in the art.

Also, when the curable composition of the present invention is prepared directly in a reaction vessel, it can be prepared by subjecting 4,4'-bis(methacryloylthio)-diphenylsulfide represented by the above formula (I) to be used as the component (A) and a polythiol represented by the above formula (II) to be used as the component (B)(ii) to addition reaction in the another polymerizable monomer to be used as the component B(i) in the presence of a base catalyst.

The components (A), (B)(ii), the base catalyst and the amount of the base catalyst employed are the same as when previously synthesizing the prepolymer having a polythioether skeleton as described above.

When carrying out the addition reaction of the components (A) and (B)(ii), as when previously synthesising the prepolymer having a polythioether skeleton as described above, the functional group equivalent ratio of the mercapto groups of the component (B)(ii) to the methacryloyl groups of the component (A) is preferably from 0.02 to 1.01, particularly from 0.05 to 0.60. When the functional group equivalent ratio of the mercapto groups of the component (B)(ii) to the methacryloyl groups of the component (A) is less than 0.02, the cured product is brittle and cannot provide a sufficient impact resistance. On the other hand, when the functional group equivalent ratio is greater than 1.01, problems arise such as a lower stability of the composition due to the unreacted mercapto groups, excessive elevation of the composition viscosity, and a nonhomogeneity of the cured product due to a nonuniformization of the polymerization reaction.

Other polymerizable monomers to be used during the addition reaction between the components (A) and (B)(ii) are not particularly limited, provided that they can be polymerized in the presence of conventional radical polymerization initiators, but from the standpoint of the reaction control, they are preferably unreactive or reactive with difficultly with the component (B)(ii) in the presence of a base catalyst, i.e., have substantially no reactivity with the component (B)(ii), and are curable with radical polymerization initiators. Specific examples include aromatic vinyl monomers such as styrene, α-methylstyrene, a-ethylstyrene, methylstyrene, ethylstyrene, chlorostyrene, bromostyrene, 2,4-dichlorostyrene, 2-chloro-4-methylstyrene, divinylbenzene, divinylbiphenyl and the like.

These aromatic vinyl monomers may be also used in mixtures of two or more kinds thereof.

When carrying out the addition reaction of the components (A) and (B)(ii), the amount of other polymerizable monomers used as the component (B)(i) is preferably 10 to 70% by weight, more preferably 15 to 50% by weight of the total amount of the components (A) and (B) and other polymerizable monomers. When the amount of other polymerizable monomers is less than 10% by weight, a composition with a high viscosity is obtained, which is difficult to handle in production when applied in industry, and when more than 70% by weight, a high refractive characteristic possessed by the component (A) cannot be obtained.

When preparing the curable composition directly in a reaction vessel, the addition reaction conditions such as the addition reaction temperature, and the conditions when removal of the base catalyst for the addition reaction is required, may be the same as when previously synthesising the prepolymer having a polythioether skeleton.

The structure of the curable composition containing the prepolymer having a polythiol skeleton thus obtained has molecular terminal ends in the composition capped with polymerizable vinyl groups, and has a very good storage stability.

In the curable composition, if necessary, other polymerizable monomers copolymerizable with the prepolymer having a polythioether skeleton as described above may be also formulated therein.

The curable composition of the present invention, different from a composition comprising a mere mixture of 4,4'-bis(methacryloylthio)diphenylsulfide, a polythiol and another polymerizable monomer, which has the problems of a poor stability and homogeneity of the cured product obtained therefrom, is extremely stable without gelling, has substantially no elevation of the viscosity even when left to stand at room temperature for 20 hours or longer, and the cured product obtained by curing the curable composition has a very good optical uniformity.

The second curable composition of the present invention can be cured by radical polymerization as in the first curable composition. The radical polymerization initiator to be used in radical polymerization may be any radical polymerization which can form radicals by heat, microwaves, IR-rays or UV-rays, and can be selected from the above-exemplified compounds depending on the use and purpose of the curable composition.

The amount of the radical polymerization initiator varies depending on the kind of the radical polymerization initiator, the use of the curable composition, and the kinds and composition ratio of the monomers charged, and therefore, cannot be determined unconditionally, but preferably is from 0.001 to 20 mole %, based on the total amount of the components (A), (B)(i) and (B)(ii), more preferably from 0.01 to 10 mole %. When the amount of the radical polymerization initiator is less than 0.001 mole %, substantially the polymerization does not proceed, and when the amount is over 20 mole %, not only it is uneconomical but, in some cases, foaming may occur during polymerization, or the molecular weight of the cured product obtained by polymerization may be reduced.

The first and second curable compositions of the present invention, when a light transmittance is not particularly demanded, can have various fillers formulated therein, if necessary. As the fillers to be used, glass fibers, alumina fibers, carbon fibers, and Aramide fibers, or powdery fillers such as silica, alumina, barium sulfate, and titanium oxide, may be included. Also, flame retardants, dyes, and pigments can be used in combination.

Also, in the first and second curable compositions of the present invention, if necessary, polymerization inhibitors, UV-ray absorbers, antioxidants, release agents, antistatic agents, and other additives can be added.

The polymerization temperature and the polymerization time during curing of the first and second curable compositions cannot be determined unconditionally, because they differ depending on the kind and amount of the radical polymerization initiator employed, but the polymerization temperature is preferably from 0° to 200° C., and the polymerization time from 0.5 to 50 hours.

EXAMPLES

The present invention is now described in more detail with reference to Examples and Comparative Examples.

The various physical properties of the cured products obtained in the Examples and Comparative Examples were measured according to the following methods.

(1) Refractive index:
The refractive index at 20° C. was measured by an Abbe refractometer (Shimazu Seisakusho, 3L Model).

(2) Light transmittance:
The measurement of transmittance of a light having a wavelength of 550 nm through a flat plate with a thickness of 3 mm was conducted by a spectrophotometer (Hitachi Seisakusho, 150-20 Model).

(3) Glass transition temperature (Tg):
By reading the peak (inflection point) of tanδ by a rheological measuring device (Orientech, Rheovibron DDV-II-EP Model), the glass transition temperature (Tg) of a sample (thickness 0.1 mm) was determined.

(4) Water absorption:
Using a test strip according to JIS-K-7209, a sample dried at 50° C. for 5 days under a reduced pressure was dipped in water at 100° C. for 2 hours, and the ratio of the weight gain based on the dry weight was determined.

(5) Analysis of mercapto groups (Volhard method):
To 1 to 2 g of a curable composition sample containing the polymer having a polythiol skeleton were added 10 ml of toluene and 10 ml of ethanol to dissolve the composition, and to the solution was added 10 ml of $0.1N\text{-}AgNO_3$ and excess $AgNO_3$ back titrated with $0.025N\text{-}NH_4SCN$ with an addition of iron alum indicator, to analyze the residual amount of mercapto groups, whereby the relative reduction (conversion) of the mercapto groups from charging is calculated.

(6) Analysis of methacryloyl groups:
Calculated from the reduction in relative ratio of the integrated value of the chemical shifts attributed to the methacryloyl group and the integrated value of the chemical shifts attributed to phenylproton by $^1H$-NMR (Hitachi K.K., R-24B Model).

(7) Viscosity:
The viscosity at 25° C. was measured by a B-type viscometer (Tokyo Keiki, BL Model).

(8) Storage stability:
When the curable composition containing the prepolymer having a polythioether skeleton was stored by standing in air at 40° C., that with a time of 20 hours or longer before a generation of a gel component is rated ⊙, that with a time of 10 to 20 hours as o, and that with a time of 10 hours or shorter as x.

(9) Impact resistance:
A −2 diopter lens 80 mmφ with a center thickness of 1.6 mm was molded, and an 16.30 g iron ball was permitted to fall freely from a height of 127 cm on the center thereof. A lens without change was evaluated as o, and a lens with cracks or fractures as x.

(10) Appearance of cured product:
Irregularities and the transparency of the cured product were evaluated by the naked eye, and a product observed to be colorless, transparent, and uniform was rated o.

EXAMPLE 1

Into a 500 ml four-necked flask equipped with a stirrer, a thermometer, an isobar dropping funnel, and a Dimroth condenser was charged 200 ml of distilled water, and 28.8 g (0.72 mole) of sodium hydroxide was dissolved therein. Then, under a nitrogen gas stream, 10 g (0.04 mole) of 4,4'-dimercaptodiphenylsulfide was added to the aqueous sodium hydroxide solution to be completely dissolved therein, followed by an addition of 0.4 g (1.6 mmole) of octyltrimethylammonium bromide. While cooling the solution to 10° C. or lower, a solution having 25.1 g (0.24 mole) of methacrylic acid chloride purified by distillation dissolved in 200 ml of dichloromethane was gradually added dropwise from the isobar dropping funnel. After completion of the dropwise addition, the solution was returned to room temperature and stirred for about one hour, and after completion of the reaction, the reaction mixture was transferred to a separation funnel, 500 ml of ether was added, and the organic layer was washed with saturated aqueous sodium chloride. The washing operations were repeated until the saturated aqueous sodium chloride used for washing became neutral, and the organic layer after washing was dried with an addition of anhydrous magnesium sulfate. The reaction product obtained by a concentration of the organic layer was purified by silica gel column chromatography (distillate hexane/dichloromethane=3/7 (volume ratio)) to give 10.4 g (yield 67%) of the desired 4,4'-bis(methacryloylthio)-diphenylsulfide.

The properties, the melting point, and elemental analysis values of the 4,4'-bis(methacryloylthio)diphenylsulfide obtained are shown below.

| Properties | colorless solid |
|---|---|
| Melting point | 61–61.5° C. |

-continued

| Elemental analysis | |
|---|---|
| Calcd. | C: 62.14%, H: 4.69%, S: 24.88% |
| Found | C: 62.51%, H: 4.11%, S: 24.53% |

Figure 1:
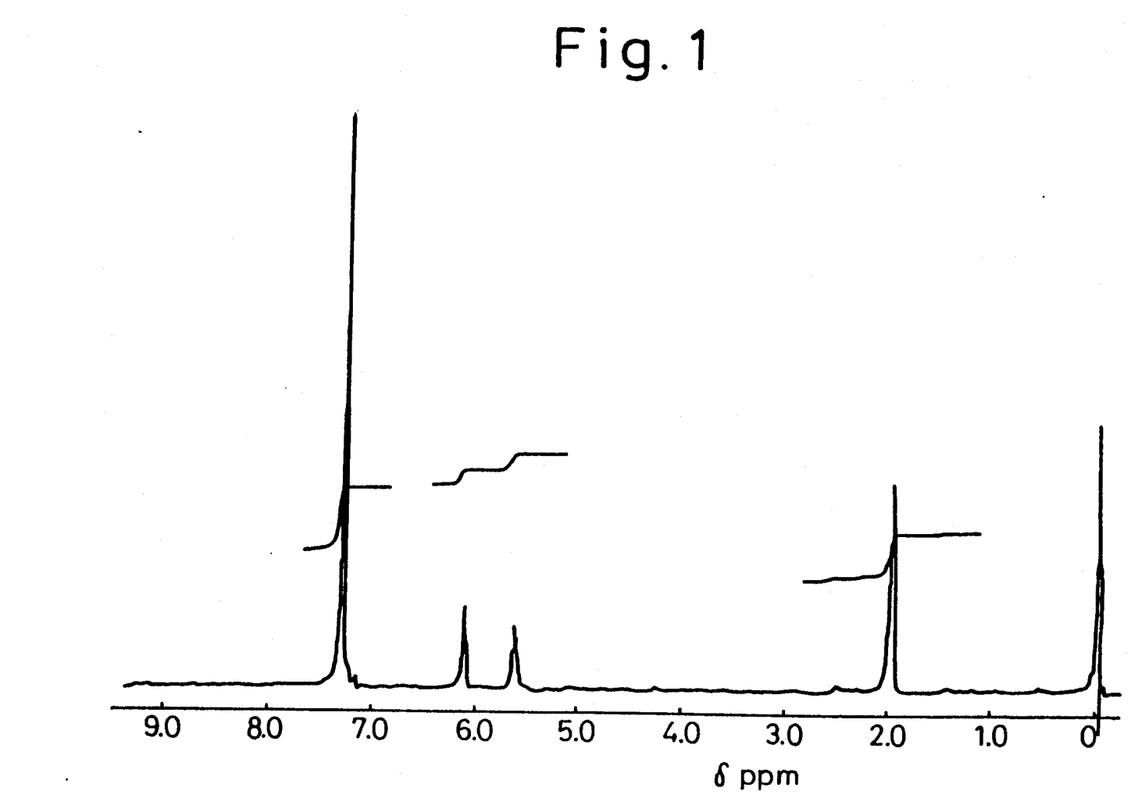
FIG. 1 is the $^1$H-NMR spectrum chart of the 4,4'-bis(methacryloylthio)diphenylsulfide obtained in Example 1.
Figure 2:
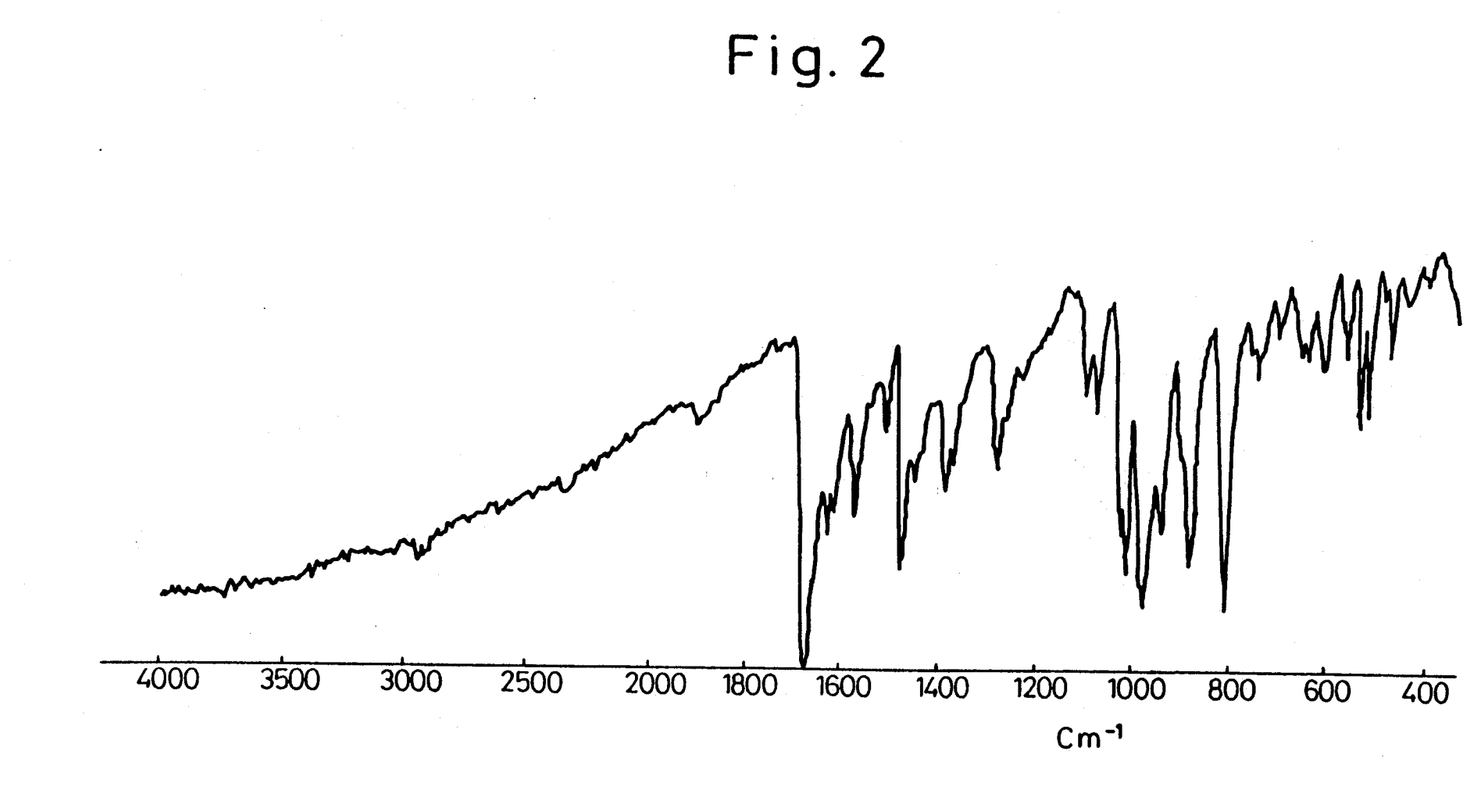
FIG. 2 is the IR spectrum chart of 4,4'-bis(methacryloylthio)diphenylsulfide obtained in Example 1.

The $^1$H-NMR spectrum (solvent CDCl$_3$, internal reference substance TMS) of the 4,4'-bis(methacryloylthio)diphenylsulfide obtained is shown in FIG. 1, and the IR-absorption spectrum in FIG. 2. The $^1$H-NMR spectrum was measured by an R-24 Model Spectrometer (60MHz) manufactured by Hitachi Seisakusho, and the IR spectrum by a 270-50 Model IR Spectrophotometer manufactured by Hitachi Seisakusho.

REFERENCE EXAMPLE 1

To 10 g of the 4,4'-bis(methacryloylthio)diphenylsulfide dimethacrylate obtained in Example 1 was added 10 mg of 1,1-bis(t-butylperoxy)-3,3,5-trimethylcyclohexane as the radical initiator, and the mixture was melted by heating at 65° C. The melt was injected into a glass plate mold, maintained at 70° C. for 5 hours, demolded by heating at a temperature elevation rate of 3° C./hour to 100° C., followed by heat curing at 150° C. for 2 hours. The cured product was colorless, transparent, and had the physical properties shown below.

| Tg | 150° C. (Orientech, Rheovibron DDV-II-FP Model) |
|---|---|
| Moisture absorption | 0.25% (ASTM D570-59T) (23° C., 24 hours dipping) |
| Refractive index | $n_D^{20}$ = 1.689 (Shimazu Seisakusho, 3L Model refractometer) |

EXAMPLE 2

In 50 g of a curable composition comprising 35 g of 4,4'-bis(methacryloylthio)diphenylsulfide and 15 g of methyl methacrylate was dissolved 0.2 g of 2,2'-azobis(2,4-dimethylvaleronitrile) as the radical polymerization initiator, the solution was injected into a glass mold 5 cm×5 cm×0.3 cm and a glass cell 0.2 mm×50 mm×20 mm, respectively, heated under a nitrogen gas stream at 35° C. for 10 hours, and then demolded by heating to 80° C. at a temperature elevation rate of 10° C./hr, followed by heat curing at 100° C. for one hour.

The obtained cured product was found to be a uniform, colorless transparent resin, and the respective values of the physical properties of the cured products are shown in Table 2.

EXAMPLES 3–11 AND COMPARATIVE EXAMPLES 1–3

Cured products were obtained by the same method as used in Example 2, except that 4,4'-bis(methacryloylthio)diphenylsulfide (A) and various vinyl monomers (B)(i) shown in Table 1 were used at the mixing ratios shown respectively in Table 2. Note, in Comparative Example 1, 2 g of isopropylperoxydicarbonate was employed instead of 2,2'-azobis(2,4-dimethylvaleronitrile). The values of the physical properties of the obtained cured products are shown in Table 2.

As apparent from Table 2, the cured products obtained by the curable compositions of the present invention have a higher refractive index and a smaller water absorption, compared with the cured products obtained in Comparative Examples 1 to 3.

TABLE 1

| Structure of vinyl monomer used in Examples and Comparative Examples | Symbols |
|---|---|
| $CH_2=\underset{\underset{CH_3}{\|}}{C}-COOCH_3$ | A |
| $CH_2=CHCOOCH_2CH_2OH$ | B |
| $CH_2=CH-\bigcirc$ | C |
| $CH_2=CH-\bigcirc-CH=CH_2$ | D |
| $CH_3CH_2C(CH_2OCO-\underset{\underset{CH_3}{\|}}{C}=CH_2)_3$ | E |
| $CH_2=CHCOOCH_2CH(OH)CH_2O-\bigcirc-\underset{\underset{CH_3}{\|}}{\overset{\overset{CH_3}{\|}}{C}}-\bigcirc-OCH_2CH(OH)CH_2OCOCH=CH_2$ | F |
| $C(CH_2OCOCH=CH_2)_4$ | G |
| $CH_2=\underset{\underset{CH_3}{\|}}{C}-CO(OCH_2CH_2)_n OCO-\underset{\underset{CH_3}{\|}}{C}=CH_2$  n = 1 | H |
|  n = 3 | I |

TABLE 1-continued

| Structure of vinyl monomer used in Examples and Comparative Examples | Symbols |
|---|---|
| $CH_2=CH-CO+OCH_2CH_2\!\!+\!\!_2O-\!\!\bigcirc\!\!-\overset{CH_3}{\underset{CH_3}{C}}-\!\!\bigcirc\!\!-O+CH_2CH_2O\!\!+\!\!_2COCH=CH_2$ | J |

TABLE 2

| Example No. | Composition monomer (A) | (B)(i) | Mixing weight ratio (A)/(B)(i) | Refractive index | Transmittance (%) | Tg (°C.) | Water absorption (%) |
|---|---|---|---|---|---|---|---|
| Example 2 | MPSDMA | A | 7/3 | 1.620 | 89 | 142 | 0.53 |
| Example 3 | | B | 7/3 | 1.625 | 89 | 140 | 0.55 |
| Example 4 | | C | 8/2 | 1.661 | 87 | 154 | 0.25 |
| Example 5 | | D | 6/4 | 1.650 | 88 | 143 | 0.35 |
| Example 6 | | E | 7/3 | 1.637 | 89 | 171 | 0.55 |
| Example 7 | | F | 6/4 | 1.648 | 88 | 170 | 0.41 |
| Example 8 | | G | 6/4 | 1.631 | 89 | 177 | 0.60 |
| Example 9 | | H | 5/5 | 1.602 | 89 | 158 | 0.65 |
| Example 10 | | I | 3/7 | 1.590 | 90 | 145 | 0.70 |
| Example 11 | | J | 1/9 | 1.596 | 90 | 150 | 0.45 |
| Comp. Ex. 1 | CR-39 | | 0/10 | 1.498 | 92 | 90 | 1.05 |
| Comp. Ex. 2 | A | | 0/10 | 1.490 | 92 | 100 | 1.30 |
| Comp. Ex. 3 | B | | 0/10 | 1.486 | 92 | 55 | 1.47 |

MPSDMA: 4,4'-Bis(methacryloylthio)diphenylsulfide
CR-39: Diethylene glycol diallylcarbonate

EXAMPLE 12

In a mixture comprising 10.0 g (0.026 mole) of 4,4'-bis(methacryloylthio)diphenylsulfide dimethacrylate, which is the component (A), and 6.3 g (0.013 mole) of pentaerythritol tetrakis(3-mercaptopropionate), which is the component (B)(ii), 81.5 mg (0.3 mmole) of 2,2'-azobis(2,4-dimethylvaleronitrile) was dissolved as the radical polymerization initiator to obtain a curable composition. In this curable composition, the value of functional group equivalent ratio of the polythiol, which is the component (B)(ii), to 4,4'-bis(methacryloylthio)-diphenylsulfide, which is the component (A), is 1.00. The curable composition was injected into a Pyrex glass mold 5 cm × 5 cm × 0.3 cm, heated under a nitrogen gas stream at 35° C. for 10 hours, and then demolded by heating up to 80° C. at a temperature elevation rate of 10° C./hr, followed by heat curing at 100° C. for one hour, to obtain a transparent cured product shaped as a plate.

The cured product obtained was found to be a uniform, colorless transparent resin. The values of the respective physical properties of the cured product are shown in Table 4.

EXAMPLES 13-17 AND COMPARATIVE EXAMPLES 4-6

Cured products were obtained by same method as in Example 12, except that 4,4'-bis(methacryloylthio)-diphenylsulfide, which is the component (A), and the polythiol, which is the component (B)(ii), shown in Table 3, were used as shown in Table 4. The values of the physical properties of the cured products are shown in Table 4.

As apparent from Table 4, the cured products obtained by the curable compositions of the present invention have a higher refractive index and a smaller water absorption, compared with the cured products obtained in Comparative Examples 4-6.

TABLE 3

| Structure of polythiols which are the component (B) (ii) used in Examples and Comparative Examples | Symbols |
|---|---|
| $C+CH_2O\overset{O}{\overset{\|}{C}}CH_2CH_2SH)_4$ | A |
| $HSCH_2\overset{O}{\overset{\|}{C}}OCH_2CH_2O\overset{O}{\overset{\|}{C}}CH_2SH$ | B |
| $HSCH_2CH_2SCH_2CH_2SH$ | C |
| $CH_3-C+CH_2O\overset{O}{\overset{\|}{C}}CH_2CH_2SH)_3$ | D |
| (benzene ring with two SH groups) | E |

TABLE 4

| No. | Component (A) | (B)(ii) | Functional group equivalent ratio (B)(ii)/(A) | $n_D$ | Water absorption (%) | Light transmittance (%) |
|---|---|---|---|---|---|---|
| Example 12 | MPSDMA 1) (0.026 mol) | A (0.013 mol) | 1.00 | 1.658 | 0.65 | 88 |
| Example 13 | MPSDMA (0.026 mol) | A (0.007 mol) | 0.27 | 1.669 | 0.60 | 87 |
| Example 14 | MPSDMA (0.026 mol) | B (0.003 mol) | 0.12 | 1.680 | 0.53 | 87 |

TABLE 4-continued

| No. | Component (A) | Component (B)(ii) | Functional group equivalent ratio (B)(ii)/(A) | $n_D$ | Water absorption (%) | Light transmittance (%) |
|---|---|---|---|---|---|---|
| Example 15 | MPSDMA (0.026 mol) | C (0.001 mol) | 0.04 | 1.685 | 0.51 | 86 |
| Example 16 | MPSDMA (0.026 mol) | D (0.013 mol) | 0.33 | 1.660 | 0.62 | 87 |
| Example 17 | MPSDMA (0.026 mol) | E (0.020 mol) | 0.77 | 1.720 | 0.47 | 85 |
| Comp. Ex. 4 | MPSDMA (0.026 mol) | B (0.00012 mol) | 0.0003 | 1.690 | Brittle and not determinable | 86 |
| Comp. Ex. 5 | MPSDMA (0.026 mol) | E (0.039 mol) | 1.5 | Not curable | Not determinable | Not determinable |
| Comp. Ex. 6 | IG 2) (0.026 mol) | A (0.010 mol) | 0.77 | 1.547 | 1.01 | 91 |

1) MPSDMA: 4,4'-Bis(methacryloylthio)diphenylsulfide
2) IG: Ethylene glycol dimethacrylate

EXAMPLE 18

In 50 g of a mixture comprising 30 g (77.6 mmole) of 4,4'-bis(methacryloyl)diphenylsulfide of the component (A), 15 g (150 mmole) of methyl methacrylate of the component (B)(i) and 5 g (10.2 mmole) of a polythiol represented by the symbol K in Table 2, 0.2 g of 2,2'-azobis(2,4-dimethylvaleronitrile) was dissolved as the radical polymerization initiator to obtain a curable composition. The curable composition was injected into a glass mold 5 cm×5 cm×0.3 cm and a glass cell 0.2 mm×50 mm×20 mm, heated under a nitrogen gas stream at 35° C. for 10 hours, and then demolded by heating to 80° C. at a temperature elevation rate of 10° C./hr, followed by heat curing at 100° C. for one hour, to obtain a transparent cured product shaped as a plate. The cured product obtained was found to be a uniform, colorless transparent resin. The respective physical properties values of the cured product are shown in Table 7.

EXAMPLES 19-27 AND COMPARATIVE EXAMPLES 7-11

Cured products were obtained by the same method as in Example 18 except for using 4,4'-bis(methacryloyl)-diphenylsulfide of the component (A), the vinyl monomer of the component (B)(i) shown in Table 5 and the polythiol of the component (B)(ii) shown in Table 6 at the respective ratios as shown in Table 7. In Comparative Example 9, 2 g of isopropylperoxydicarbonate was used instead of 2,2'-azobis(2,4-dimethylvaleronitrile). The values of the physical properties of the cured products obtained are shown in Table 7.

TABLE 5

| Vinyl monomer of component (B) (i) used in Examples and Comparative Examples | Symbols |
|---|---|
| $CH_2=\underset{\underset{CH_3}{\mid}}{C}-COOCH_3$ | A |
| $CH_2=CHCOOCH_2CH_2OH$ | B |
| $CH_2=CH-C_6H_5$ | C |
| $CH_2=CH-C_6H_4-CH=CH_2$ | D |
| $CH_3CH_2C(CH_2OCO-\underset{\underset{CH_3}{\mid}}{C}=CH_2)_3$ | E |
| $CH_2=CHCOOCH_2CH(OH)CH_2O-C_6H_4-C(CH_3)_2-C_6H_4-OCH_2CH(OH)CH_2OCOCH=CH_2$ | F |
| $C(CH_2OCOCH=CH_2)_4$ | G |
| $CH_2=\underset{\underset{CH_3}{\mid}}{C}-CO(OCH_2CH_2)_n OCO-\underset{\underset{CH_3}{\mid}}{C}=CH_2 \quad n=1$ | H |
| $n=3$ | I |

TABLE 5-continued

Vinyl monomer of component (B) (i) used in Examples and Comparative Examples | Symbols
--- | ---
 | J

TABLE 6

Polythiols of Component (B) (ii) used in Examples and Comparative Examples | Symbols
--- | ---
C(CH₂OCOCH₂CH₂SH)₄ | K
HSCH₂CH₂SCH₂CH₂SH | L
HSCH₂COCH₂CH₂OCCH₂SH | M
CH₃—CH₂—C(CH₂OCOCH₂CH₂SH)₃ | N
benzene-1,2-dithiol (o-SH, SH) | O

TABLE 7

| No. | Monomer component (A) | (B)(i) | (B)(ii) | Weight mixing ratio (A)/(B)(i)/(B)(ii) | Functional group equivalent ratio of component (B)(ii) to component (A) | Refractive index | Light transmittance (°C.) | Tg (°C.) | Water absorption (%) |
| --- | --- | --- | --- | --- | --- | --- | --- | --- | --- |
| Example 18 | MPSDMA | A | K | 6/3/1 | 0.26 | 1.613 | 89 | 127 | 0.60 |
| Example 19 | " | B | | 6/3/1 | 0.26 | 1.615 | 89 | 135 | 0.43 |
| Example 20 | " | C | L | 6/3/1 | 0.42 | 1.649 | 87 | 155 | 0.35 |
| Example 21 | " | D | | 4/5/1 | 0.63 | 1.630 | 87 | 157 | 0.31 |
| Example 22 | " | E | M | 6/3/1 | 0.31 | 1.610 | 89 | 132 | 0.30 |
| Example 23 | " | F | | 4/5/1 | 0.46 | 1.608 | 89 | 140 | 0.50 |
| Example 24 | " | G | N | 4/4/2 | 0.73 | 1.577 | 90 | 133 | 0.52 |
| Example 25 | " | H | | 4/4/2 | 0.73 | 1.577 | 90 | 130 | 0.49 |
| Example 26 | " | I | O | 4/5/1 | 0.67 | 1.589 | 90 | 127 | 0.43 |
| Example 27 | " | J | | 5/4/1 | 0.54 | 1.638 | 89 | 131 | 0.39 |
| Comp. Ex. 7 | " | A | K | 0.4/9.5/0.1 | 0.40 | 1.507 | 92 | 110 | 1.25 |
| Comp. Ex. 8 | " | A | | 2/1/7 | 5.54 | 1.566 | Not determinable due to poor molding | | |
| Comp. Ex. 9 | — | CR-39 | — | 0/10/0 | — | 1.498 | 92 | 90 | 1.05 |
| Comp. Ex. 10 | — | A | — | 0/10/0 | — | 1.490 | 92 | 100 | 1.30 |
| Comp. Ex. 11 | — | B | — | 0/10/0 | — | 1.486 | 92 | 55 | 1.47 |

MPSDMA: 4,4'-Bis(methacryloylthio)diphenylsulfide
CR-39: Diethylene glycol diallylcarbonate

EXAMPLE 28

A 2-liter separate flask was set with a stirrer and a dropping funnel and charged with 500 g of 4,4'-bis(methacryloylthio)diphenylsulfide at room temperature, which was then dissolved in 600 ml of distilled dichloromethane. Then, while stirring under a nitrogen gas stream, 0.8 g of diethylamine was added at room temperature, and subsequently, 50 g of ethylene glycol dithioglycolate was dropwise added. The reaction temperature was controlled to 25° C. -35° C., and stirring was continued for 3 hours to complete the reaction. The completion of the reaction was judged by confirming the disappearance of mercapto group, in an analysis of the mercapto group by the Volhard method. After completion of the reaction, dimethylamine was removed by an addition of 50 g of an inorganic adsorbent, for a strong base adsorption (Kyowa Kagaku Kogyo K.K., Kyoward 700 SL) and after the absorbent was filtered off, the mixture was concentrated under a reduced pressure to give a liquid high viscosity syrup. At this point, the conversion of methacryloyl groups was calculated from the reduction in chemical shift peaks attributed to the methacryloyl groups, by $^1$H-NMR spectrum, and an amount of 400 g of this liquid was diluted with 182 g of styrene to give a low viscosity composition. The results are shown in Table 8.

EXAMPLE 29

A 2-liter separable flask was set with a stirrer and a dropping funnel and charged with 500 g of 4,4'-bis(methacryloylthio)diphenylsulfide and 250 g of styrene at room temperature, followed by vigorous stirring to effect dissolution. Then, while stirring under a nitrogen gas stream, 0.8 g of diethylmethylamine was added at room temperature, and subsequently, 50 g of ethylene glycol dithioglycolate was added dropwise by the dropping funnel. The reaction temperature was controlled to 25° C.-35° C. Then, stirring was continued for 3 hours to complete the reaction, and completion of the reaction was judged by confirming the reduction in chemical shift peaks attributed to methacryloyl groups in $^1$H-NMR spectrum and disappearance of mercapto group in analysis of mercapto group by the Volhard method. After completion of the reaction, dimethylamine was removed by addition of 40 g of an inorganic adsorbent for a strong base adsorption (Kyowa Kagaku Kogyo K.K., Kyoward 700 SL), and the adsorbent was filtered off to give a liquid product. The results are shown in Table 8.

EXAMPLES 30-36 AND COMPARATIVE EXAMPLES 12-13

The addition reaction was carried out by the same procedure as in Example 28, except for mixing 4,4'-bis(-methacryloylthio)diphenylsulfide of the component (A), polythiols of the component (B)(ii), polymerizable monomers of the component (B)(i), and base catalysts at the ratios shown in Table 8. The results are shown in Table 8.

physical properties of these cured products are shown in Table 9.

COMPARATIVE EXAMPLES 14-15

The polymerization was carried out by the same method as in Example 37 except for using the curable compositions obtained in Comparative Examples 12 and 13 to obtain the cured products, respectively. The values of the physical properties of these cured products are shown in Table 9.

TABLE 8

| No. | Monomer component (A) | (B)(i) | (B)(ii) | Mixing weight (g) (A)/(B)(i)/(B)(ii) | Preliminary polymerization catalyst Kind | Amount added (g) | Preliminary polymerization catalyst (%) Methacryloyl group | Mercapto group | Viscosity (cp) | Storage stability | Functional group equivalent ratio of component (B) to component (A) |
|---|---|---|---|---|---|---|---|---|---|---|---|
| Example 28 | MPSDMA | St | TOS-21 | 500/250/50 | Diethylmethylamine | 0.8 | 21 | 100 | 80 | o | 0.18 |
| Example 29 | " | " | TOS-21 | 500/250/50 | Diethylmethylamine | 0.8 | 22 | 100 | 88 | o | 0.18 |
| Example 30 | " | " | DMB | 500/250/50 | Diethylmethylamine | 0.8 | 28 | 100 | 38 | o | 0.27 |
| Example 31 | " | " | DMES | 500/250/50 | Diethylmethylamine | 0.8 | 26 | 99 | 35 | o | 0.13 |
| Example 32 | " | " | KOS-4 | 500/250/25 | Diethylmethylamine | 0.5 | 10 | 100 | 300 | o | 0.09 |
| Example 33 | " | CSt | DME | 500/250/50 | Triethylamine | 1.0 | 42 | 99 | 31 | o | 0.27 |
| Example 34 | " | DVB | DMES | 500/250/50 | " | 0.8 | 28 | 99 | 28 | o | 0.25 |
| Example 35 | " | " | POS-306 | 500/250/25 | Dimethylethylamine | 0.8 | 7 | 98 | 220 | o | 0.08 |
| Example 36 | " | DVBP | DMES | 500/250/50 | Diethylamine | 0.8 | 26 | 100 | 31 | o | 0.25 |
| Comp. Ex. 12 | " | St | TOS-21 | 500/250/3 | Diethylamine | 0.8 | 3 | 98 | 15 | o | 0.01 |
| Comp. Ex. 13 | 1 G | " | KOS-4 | 730/0/270 | " | 1.0 | 34 | 99 | 280 | o | — |

Remarks
MPSDMA: 4,4'-bis(methacryloylthio)diphenylsulfide
1G: ethylene glycol dimethacrylate
St: styrene
CSt: p-chlorostyrene
DVB: divinylbenzene
DVBP: 3,3'-divinylbiphenyl
DMES: bis(2-mercaptoethyl)sulfide
DMB: 1,2-dimercaptobenzene
TOS-21: ethylene glycol dithioglycolate
KOS-4: pentaerythritol tetrathioglycolate
POS-306: 1,1,1-trimethylolpropane trithiopropionate

EXAMPLE 37

One hundred (100) parts by weight of the curable composition obtained in Example 28 were mixed with 0.3 part by weight of azobisisobutyronitrile, and the resulting solution was injected into glass molds 70 mmφ×3 mm and 70 mmφ×0.1 mm, respectively. These cast moldings were maintained in a hot air furnace at 35° C. for 6 hours, the temperature elevated to 80° C. over 5 hours, followed by curing by maintaining at 80° C. for 2 hours. After demolding, an annealing treatment was applied at 100° C. for 2 hours. The physical properties of the cured products are shown in Table 9.

EXAMPLES 38-41

Polymerization was carried out by the same method as in Example 37 except for using the curable compositions containing the prepolymer having a polythioether skeleton obtained in Examples 30, 32, 34 and 36 to obtain the cured products, respectively. The values of the physical properties of these cured products are shown in Table 9.

COMPARATIVE EXAMPLE 16

The polymerization was carried out according to the same method as in Example 37 except for using a composition comprising 3 parts by weight of diisopropylperoxy dicarbonate formulated in 100 parts by weight of diethylene glycol bisallylcarbonate to obtain a cured product. The results are shown in Table 9.

As apparent from Table 9, compared with Examples 37-41, Comparative Examples 15-16 exhibit a high absorption.

Therefore, it can be seen that the cured product obtained by curing the curable composition of the present invention has a high refractive index, and superior characteristics such as a very good optical uniformity, heat resistance, low water absorption, and impact resistance. Also, as apparent from Table 8, the curable composition of the present invention has a very good storage stability and can be set at a low viscosity by controlling the formulation ratio of the composition.

TABLE 9

| No. | Refractive index | Light transmittance (%) | Glass transition temperature (°C.) | Water absorption (%) | Impact resistance | Appearance of cured product | Curable composition used |
| --- | --- | --- | --- | --- | --- | --- | --- |
| Example 37 | 1.648 | 87 | 175 | 0.35 | o | o | Example 28 |
| Example 38 | 1.665 | 87 | 180 | 0.33 | o | o | Example 30 |
| Example 39 | 1.658 | 87 | 170 | 0.45 | o | o | Example 32 |
| Example 40 | 1.651 | 87 | 175 | 0.35 | o | o | Example 34 |
| Example 41 | 1.673 | 86 | 170 | 0.36 | o | o | Example 36 |
| Comp. Ex. 14 | 1.656 | 87 | 195 | 0.32 | x | o | Comp. Ex. 12 |
| Comp. Ex. 15 | 1.529 | 92 | 80 | 1.07 | o | o | Comp. Ex. 13 |
| Comp. Ex. 16 | 1.498 | 92 | 90 | 1.05 | o | o | — |

INDUSTRIAL APPLICABILITY

As stated above, the 4,4'-bis(methacryloylthio)diphenylsulfide of the present invention not only has a high polymerizability but also a very good compatibility and copolymerizability with other polymerizable monomers having an olefinic double bond. Also, the cured product obtained by a polymerization curing of the 4,4'-dimercaptodiphenylsulfide dimethacrylate alone has not only a high heat resistance and low water absorption, but also an extremely high refractive index ($n_D^{20} = 1.689$). Therefore, the 4,4'-bis(methacryloylthio)-diphenylsulfide of the present invention is an extremely useful and novel polymerizable monomer in the fields of paints, adhesives, cast molding materials, and photosensitive materials, and can be applied to high refractive index transparent resins by utilizing the high refractive index thereof.

Furthermore, curable compositions of the present invention not only have a very good curability, but also the compositions obtained by curing the curable compositions of the present invention have specific physical properties such as a very good optical uniformity and a high refractive index, and moreover, a high heat resistance and low water absorption, and therefore, are particularly useful in an industrial field such as optical materials, and in industrial fields such as coating agents, sealing agents, paints, and adhesives.

We claim:

1. A method of producing a curable composition containing a prepolymer having a polythioether skeleton comprising addition reacting (A) 4,4'-bis (methacryloylthio)diphenylsulfide having the formula (I):

and (B) (ii) a polythiol having the formula (II):

wherein R is a polyvalent organic group comprising an aliphatic or aromatic hydrocarbon and n represents an integer of 2 or more, with the functional group equivalent ratio of the mercapto groups of the component (B) (ii) to the methacryloyl groups of the component (A) being from 0.02 to 1.01, with at least one other vinyl monomer selected from the group consisting of aromatic vinyl compounds, unsaturated fatty acids and derivatives thereof, unsaturated dibasic acids and derivatives thereof, and vinyl cyanide compounds, said at least one other vinyl monomer being copolymerizable with said 4,4'-bis (methacryloylthio)diphenylsulfide in the presence of a base catalyst.

2. The method as claimed in claim 1, wherein said polythiols having the formula (II) are aliphatic polythiols or aromatic polythiols having $n = 2-5$ in the formula (II).

3. The method as claimed in claim 1, wherein said at least one other vinyl monomer is an unsaturated fatty acid ester.

4. The method as claimed in claim 1, wherein said at least one other vinyl monomer is at least one compound selected from the group consisting of styrene, α-methylstyrene, α-ethylstyrene, methylstyrene, ethylstyrene, chlorostyrene, bromostyrene, 2,4-dichlorostyrene, 2-chloro-4-methylstyrene, divinylbenzene and divinylbiphenyl.

* * * * *